(12) United States Patent
Murai et al.

(10) Patent No.: US 9,181,174 B2
(45) Date of Patent: Nov. 10, 2015

(54) METHOD FOR ISOLATING TERTIARY AMINO ALCOHOL

(71) Applicant: KABUSHIKI KAISHA TOSHIBA, Minato-ku (JP)

(72) Inventors: Shinji Murai, Sagamihara (JP); Takehiko Muramatsu, Yokohama (JP); Daigo Muraoka, Suginami-ku (JP); Satoshi Saito, Yamato (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 0 days.

(21) Appl. No.: 14/219,419

(22) Filed: Mar. 19, 2014

(65) Prior Publication Data
US 2014/0296576 A1 Oct. 2, 2014

(30) Foreign Application Priority Data

Mar. 27, 2013 (JP) ................. 2013-066605

(51) Int. Cl.
*C07C 213/10* (2006.01)
*B01D 53/14* (2006.01)
(52) U.S. Cl.
CPC .......... *C07C 213/10* (2013.01); *B01D 53/1425* (2013.01); *B01D 53/1456* (2013.01); *B01D 53/1493* (2013.01); *B01D 2252/20431* (2013.01); *B01D 2252/20478* (2013.01); *Y02C 10/06* (2013.01)

(58) Field of Classification Search
CPC ...................................... C07C 213/10
USPC .................. 564/497, 498, 499, 437
See application file for complete search history.

(56) References Cited

U.S. PATENT DOCUMENTS 6,353,138 B1 * 3/2002 Rooney ............ 564/497
2010/0130715 A1 5/2010 Grigsby, Jr. et al.

FOREIGN PATENT DOCUMENTS

JP 2000-26381 1/2000
WO WO 00/69807 A1 11/2000

OTHER PUBLICATIONS

Extended European Search Report issued Sep. 3, 2014, in European Patent Application No. 14161078.2.

* cited by examiner

*Primary Examiner* — Brian J Davis
(74) *Attorney, Agent, or Firm* — Oblon, McClelland, Maier & Neustadt, L.L.P.

(57) ABSTRACT

A method for isolating an amino alcohol simply from an amino alcohol aqueous solution containing a heterocyclic amine compound is provided. The method is a method for isolating a tertiary amino alcohol from a tertiary amino alcohol aqueous solution containing a heterocyclic amine compound, and for generating an enamine by adding a ketone to the tertiary amino alcohol aqueous solution, isolating the enamine from the tertiary amino alcohol aqueous solution, and isolating the tertiary amino alcohol from a residual liquid obtained by isolating the enamine.

10 Claims, No Drawings

METHOD FOR ISOLATING TERTIARY AMINO ALCOHOL

CROSS REFERENCE TO RELATED APPLICATION

This application is based upon and claims the benefit of priority from Japanese Patent Application No. 2013-066605, filed on Mar. 27, 2013; the entire contents of which are incorporated herein by reference.

FIELD

Embodiments described herein relate generally to a method for isolating a tertiary amino alcohol.

BACKGROUND

A greenhouse effect due to increase of a carbon dioxide ($CO_2$) concentration is recently pointed out as a cause of a global warming phenomenon, and there is an urgent need for an international countermeasure for protecting an environment on a global basis. A major source of $CO_2$ generation is an industrial activity and momentum is rising to inhibit its emission.

As acid gas separation technology for inhibiting concentration rise of an acid gas such as $CO_2$, a method (absorption method) where the acid gas is absorbed by using a chemical absorbent and recovered is studied. For example, in a facility such as a thermal power plant in which a fossil fuel (coal, petroleum, natural gas, etc.) is used, by bringing an exhaust gas generated at a time of combustion of the fossil fuel into contact with the chemical absorbent, removal and recovery of $CO_2$ in a combustion exhaust gas is performed.

As the chemical absorbent used in the absorption method, it is tried to use alkanolamines. In particular, an amino alcohol aqueous solution which contains a heterocyclic amine compound exhibits an excellent $CO_2$ absorbability.

Demand for a separation and recovery processing of an acid gas such as $CO_2$ tends to increase more and more in recent years, and it is tried to recover a chemical absorbent having been used in a recovery processing of $CO_2$ and to use the chemical absorbent again. However, if the absorbent after being used in the recovery processing of $CO_2$ is used again as it is, corrosion in a contact region is apt to be caused in a plant facility, for example, and there is a possibility that a life duration of the entire facility is reduced. Thus, technology to separate and recover an amino alcohol from an absorbent having been used in a recovery processing of $CO_2$ is demanded.

On the other hand, in a case where an amino alcohol is to be isolated from an amino alcohol aqueous solution containing a heterocyclic amine compound, as the heterocyclic amine compound being apt to evaporate and a vacuum state being hard to be obtained, separation and purification of the amino alcohol and the heterocyclic amine compound is difficult by a purification method such as distillation. Thus, it is difficult to isolate an amino alcohol at a high purity from an amino alcohol aqueous solution containing a heterocyclic amine compound.

As an isolation method of an amino alcohol, there is suggested a method for isolating the amino alcohol or an acid addition salt of the amino alcohol from an amino alcohol aqueous solution. However, an effective means is not yet found for a method for isolating an amino alcohol from an amino alcohol aqueous solution containing a heterocyclic amine compound.

DETAILED DESCRIPTION

An isolation method of a tertiary amino alcohol of an embodiment is a method for isolating the tertiary amino alcohol from a tertiary amino alcohol aqueous solution containing a heterocyclic amine compound, and has generating an imine and/or enamine by adding an aldehyde and/or ketone to the tertiary amino alcohol aqueous solution, and isolating the tertiary amino alcohol after isolating the imine and/or enamine from the tertiary amino alcohol aqueous solution.

Hereinafter, an embodiment will be described in detail. An isolation method of a tertiary amino alcohol of the embodiment is a method for isolating a tertiary amino alcohol from a tertiary amino alcohol aqueous solution containing a heterocyclic amine compound, and has generating an imine and/or enamine by adding an aldehyde and/or ketone to the tertiary amino alcohol aqueous solution; and isolating the tertiary amino alcohol after isolating the imine and/or enamine from the tertiary amino alcohol aqueous solution.

As the tertiary amino alcohol, a tertiary amino alcohol represented by a following general formula (1) can be used.

[chemical formula 1]

($R^1$, $R^2$ and $R^3$ indicate hydrocarbon groups having 1 to 6 carbon atoms, and may be the same or different from each other, and at least one of $R^1$, $R^2$ and $R^3$ is the hydrocarbon group having a hydroxyl group.)

When the number of carbon atoms of $R^1$, $R^2$ or $R^3$ exceed 6, the tertiary amino alcohol is hard to be dissolved in water, and there is a possibility that a stable solution cannot be obtained.

As the tertiary amino alcohol, there are concretely cited, for example: N, N-dimethylaminoethanol; N, N-diethylaminoethanol; N-ethyl-N-methylaminoethanol; N-butyl-N-methylaminoethanol; N-hexyl-N-methylaminoethanol; N, N-dimethylamino-1-propanol; N, N-diethylamino-1-propanol; N-ethyl-N-methylamino-1-propanol; N-butyl-N-methylamino-1-propanol; N-hexyl-N-methylamino-1-propanol; N, N-dimethylamino-1-butanol, N, N-diethylamino-1-butanol; N-ethyl-N-methylamino-1-butanol; N-butyl-N-methylamino-1-butanol; N-hexyl-N-methylamino-1-butanol; N-methyldiethanolamine; N-ethyldiethanolamine; N-propyldiethanolamine; N-butlydiethanolamine; N-methyl-N-(3-hydroxypropyl)ethanolamine; N-ethyl-N-(3-hydroxypropyl)ethanolamine; N-methyl-dipropanolamine; N-methyl-N-(3-hydroxypropyl)propanolamine; N-ethyl-N-(3-hydroxypropyl)propanolamine; N-methyl-dibutanolamine; N-methyl-N-(3-hydroxypropyl)butanolamine; N-ethyl-N-(3-hydroxypropyl)butanolamine, and so on.

As the heterocyclic amine compound, there are cited: azetidine; 1-methylazetidine; 1-ethylazetidine; 2-methylazetidine; 2-azetidylmethanol; 2-(2-aminoethyl)azetidine; pyrrolidine; 1-methylpyrrolidin; 2-methylpyrrolidin; 2-butylpyrrolidine; 2-pyrrolidylmethanol; 2-(2-aminoethyl)pyrrolidine; piperidine; 1-methylpiperidine; 2-ethylpiperidine; 3-propylpiperidine; 4-ethylpiperidine; 2-piperidylmethanol; 3-piperidylethanol; 2-(2-aminoethyl)pyrrolidine; hexahydro-1H-azepine; hexamethylenetetramine; piperazine; a piperazine derivative, and so on.

Among the above, at least one kind selected from the group consisting of piperidine, a piperidine derivative, piperazine and a piperazine derivative is suitably used, since an excellent effect as a reaction accelerator can be obtained when the tertiary amino alcohol aqueous solution is used as a later-described acid gas absorbent, for example.

It is more preferable that the heterocyclic amine compound is at least one kind selected from the group consisting of piperazine, 2-methylpiperazine, and 2,5-dimethylpiperazine.

The isolation method of the tertiary amino alcohol according to the embodiment can be suitably applied to a case where, for example, a tertiary amino alcohol is to be isolated and recovered from a tertiary amino alcohol aqueous solution having been used as an acid gas absorbent when the acid gas is to be removed from an exhaust gas containing the acid gas such as a carbon dioxide.

A method for removing an acid gas, for example, a carbon dioxide, from an exhaust gas containing the acid gas by using a tertiary amino alcohol aqueous solution as an acid gas absorbent can be performed by making the exhaust gas containing the carbon dioxide contact the tertiary amino alcohol aqueous solution so that the tertiary amino alcohol aqueous solution absorbs the carbon dioxide (carbon dioxide absorption process step), and thereafter heating the tertiary amino alcohol aqueous solution in which the carbon dioxide is absorbed and which is obtained in the above-described carbon dioxide absorption process step, to desorb and recover the carbon dioxide (carbon dioxide separation process step).

A content of the tertiary amino alcohol contained in the tertiary amino alcohol aqueous solution is not particularly limited, but it is preferable the content is 15 to 50 mass % if the tertiary amino alcohol aqueous solution is used as the absorbent of the acid gas such as a carbon dioxide. By setting the content of the tertiary amino alcohol to be 15 mass % or more, sufficient absorption amount and absorption speed of the carbon dioxide can be obtained, which enables an excellent processing efficiency. Further, when the content of the tertiary amino alcohol is 50 mass % or less, deterioration of a function of water as an activator for the carbon dioxide absorption or an excessive viscosity rise of an absorbent liquid can be inhibited. Further, the tertiary amino alcohol aqueous solution having a tertiary amino alcohol content in a range of 15 to 50 mass % is not only high in carbon dioxide absorption amount and carbon dioxide absorption speed but is also high in carbon dioxide desorption amount and carbon dioxide desorption speed, and is advantageous in that the carbon dioxide can be recovered efficiently.

When the tertiary amino alcohol aqueous solution is used as the absorbent of the acid gas such as a carbon dioxide, the heterocyclic amine compound functions as a reaction accelerator and its content is not particularly limited, but it is preferable that the content is 1 to 15 mass %. When the content of the heterocyclic amine compound contained in the tertiary amino alcohol aqueous solution is less than 1 mass %, there is a possibility that an effect to improve the carbon dioxide absorption speed cannot be obtained sufficiently. When the content of the heterocyclic amine compound contained in the tertiary amino alcohol aqueous solution exceeds 15 mass %, a viscosity of the solution becomes excessively high, and there is a possibility, on the contrary, that a reactivity is reduced.

When the tertiary amino alcohol aqueous solution is used as the absorbent of the acid gas such as a carbon dioxide, the tertiary amino alcohol aqueous solution can contain, in addition to the above-described heterocyclic amine compound, alkanolamines such as 2-(isopropylamino)ethanol, 2-(ethylamino)ethanol, and 2-amino-2-methyl-1-propanol, as a reaction accelerator. In such a case, it is preferable that a content of the alkanolamines, in total with the content of the heterocyclic amine compound, is 1 to 15 mass %.

The tertiary amino alcohol aqueous solution can contain, other than the above-described amino alcohol and heterocyclic amine compound, an anticorrosive of a phosphoric acid base or the like for preventing corrosion of a plant facility, a defoamer of a silicone base or the like for preventing foaming, an antioxidant for preventing deterioration of the tertiary amino alcohol aqueous solution, and so on.

A process step of making a gas containing a carbon dioxide contact the above-described tertiary amino alcohol aqueous solution can usually be performed under almost an atmospheric pressure with a temperature of the tertiary amino alcohol aqueous solution being a room temperature to 60° C. or lower, and a method thereof is not particularly limited. For example, the process step can be performed by a method in which a gas containing a carbon dioxide is bubbled into a tertiary amino alcohol aqueous solution and absorbed, a method(atomizing or spraying method) in which a tertiary amino alcohol aqueous solution is made to fall in a form of mist in a gas flow containing a carbon dioxide, a method in which a gas containing a carbon dioxide and a tertiary amino alcohol aqueous solution are made to countercurrent-contact in an absorption tower where a filler made of a porcelain or a filler made of a metal net is supplied, and so on.

A process step of separating a carbon dioxide from a tertiary amino alcohol aqueous solution having absorbed the carbon dioxide and recovering the pure or highly concentrated carbon dioxide can usually be performed under almost an atmospheric pressure with a temperature of the tertiary amino alcohol aqueous solution being 70° C. or higher, and a method thereof is not particularly limited. For example, the process step can be performed by a method in which a tertiary amino alcohol aqueous solution is heated and foamed in a pot and desorption is done similarly to by distillation, a method in which a liquid interface is broadened and heating is done in a plate tower, a spray tower, or a regeneration tower where a filler made of a porcelain or a metal net is supplied, and so on.

A basic configuration of a method for isolating a tertiary amino alcohol has a process step (hereinafter, indicated as a process step (1)) of adding an aldehyde and/or ketone to a tertiary amino alcohol aqueous solution to generate an imine and/or enamine, and a process step (hereinafter, indicated as a process step (2)) of isolating the imine and/or enamine from the tertiary amino alcohol aqueous solution and thereafter isolating a tertiary amino alcohol.

In the process step (1), as aldehyde added to the tertiary amino alcohol aqueous solution, any aldehyde can be used as long as no hindrance is caused to a condensation reaction with a heterocyclic amine compound. As an aldehyde, for example, an aliphatic aldehyde or aromatic aldehyde having 4 to 12 carbon atoms can be used.

With regard to the aromatic aldehyde, a part of a hydrogen atom of a benzene ring can be replaced by a halogen atom or an alkyl group having 1 to 6 carbon atoms. As concrete examples of the aromatic aldehyde, there are cited, for example, benzaldehyde, p-chlorobenzaldehyde, p-methylbenzaldehyde, and so on.

As concrete examples of the aliphatic aldehyde having 4 to 12 carbon atoms, there are cited, for example, butylaldehyde, caproaldehyde, and so on. If the number of carbon atoms of the aliphatic aldehyde is smaller than 4, a chemical stability is reduced, and there is a possibility that a stable reactivity cannot be obtained. Further, if the number of carbon atoms of the aliphatic aldehyde exceeds 12, there is a possibility that a reactivity with a heterocyclic amine compound is reduced.

Further, if the number of carbon atoms of the aliphatic aldehyde exceeds 12, a boiling point of imine obtained after a reaction is heightened, and there is a possibility that separation from the tertiary amino alcohol by distillation becomes difficult. Note that use of lower aliphatic aldehyde is not very preferable since generated imine is easily polymerized.

Above all, the aromatic aldehyde is suitably used since imine obtained after a reaction with a heterocyclic amine compound is easy to be isolated from a tertiary amino alcohol.

A reaction process step of generating imine from a heterocyclic amine compound and the aldehyde is performed in a usual manner. In other words, generally, the aldehyde is added to the amino alcohol aqueous solution containing the heterocyclic amine compound and heating is done as necessary. On this occasion, it is possible to add an organic solvent such as alcohols such as methanol and ethanol, aromatic hydrocarbons such as toluene and xylene, and halogenated hydrocarbons such as chlorobenzene.

A reaction condition of the heterocyclic amine compound and the aldehyde is not particularly limited. In a reaction of the heterocyclic amine compound and the aldehyde, a reaction temperature is usually in a range of a room temperature to 100° C. and a reaction time is usually in a range of 5 minutes to 24 hours. Further, with regard to a quantity ratio of the heterocyclic amine compound contained in the tertiary amino alcohol aqueous solution and the aldehyde, usually, for 1 mol of heterocyclic amine compound, a rate of 1 to 3 mol(s) of aldehyde is preferable and a rate of 1.0 to 1.2 mol is more preferable.

The imine obtained by the above-described reaction is isolated in a usual manner. More specifically, the imine is extracted by an organic solvent such as toluene, ethyl ether, and ethyl acetate, for example. Thereafter, by an operation such as distilling off or the like of the organic solvent, the imine can be isolated easily. Further, other than by a method of extraction, the imine can be isolated by an operation such as distillation or recrystalization under a room temperature or under a reduced pressure, for example.

Note that it is preferable that water is removed from the tertiary amino alcohol aqueous solution before the above-described isolation operation of the imine Removal of water can be performed in a usual manner such as by azeotrope with benzene or the like, for example. Removal of water can be performed after generation of the imine in the tertiary amino alcohol aqueous solution, and can be performed before addition of the aldehyde in the tertiary amino alcohol aqueous solution.

The tertiary amino alcohol can be isolated by distillation or the like of the tertiary amino alcohol from a residual liquid after isolation of the imine.

In the process step (1), as the ketone added to the tertiary amino alcohol aqueous solution, the ketone represented by a following general formula (2) can be used as long as no hindrance is caused to a condensation reaction with the heterocyclic amine compound.

[chemical formula 2]

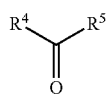

(2)

($R^4$ and $R^5$ indicate aliphatic groups or aromatic groups having 1 to 18 carbon atoms, $R^4$ and $R^5$ may be the same or different, $R^4$ and $R^5$ may be joined to form a ring structure, and at least one of $R^4$ and $R^5$ is the aliphatic group.)

If the number of carbon atoms of $R^4$ or $R^5$ exceed 18, there is a possibility that a reactivity with the heterocyclic amine compound is reduced. Further, if the number of carbon atoms of $R^4$ or $R^5$ exceed 18, a boiling point of the enamine obtained after a reaction is heightened, and there is a possibility that separation from the tertiary amino alcohol by distillation becomes difficult. It is more preferable that the number of carbon atoms of $R^4$ and $R^5$ are 1 to 6.

As concrete examples of the ketone, there are cited acetone, ethylmethylketone, diethylketone, methylisobutylketone, cyclopentanone, cyclohexanone, acetophenone, and so on.

A reaction process step of generating the enamine from the heterocyclic amine compound and the ketone is performed in a usual manner. In other words, generally, the ketone is added to the amino alcohol aqueous solution containing the heterocyclic amine compound and heating is performed as necessary. On this occasion, it is possible to add an organic solvent such as alcohols such as methanol and ethanol, aromatic hydrocarbons such as benzene, toluene, and xylene, and halogenated hydrocarbons such as chlorobenzene.

A reaction condition of the heterocyclic amine compound and the ketone is not particularly limited. In a reaction of the heterocyclic amine compound and the ketone, a reaction temperature is usually in a range of a room temperature to 100° C. and a reaction time is usually from 5 minutes to 24 hours. Further, with regard to a quantity ratio of the heterocyclic amine compound contained in the tertiary amino alcohol aqueous solution and the ketone, usually, for 1 mol of heterocyclic amine compound, a rate of 1 to 3 mol(s) of ketone is preferable and a rate of 1.0 to 1.2 mol is more preferable.

The enamine obtained by the above-described reaction is isolated in a usual manner. More specifically, the enamine is extracted by an organic solvent such as toluene, ethyl ether, and ethyl acetate, for example. Thereafter, by an operation such as distilling off or the like of the organic solvent, the enamine can be isolated easily. Further, other than by a method of extraction, the enamine can be isolated by an operation such as distillation or recrystalization under a room temperature or under a reduced pressure, for example.

Note that it is preferable that water is removed from the tertiary amino alcohol aqueous solution before the above-described isolation operation of the enamine. Removal of water can be performed in a usual manner such as by azeotrope with benzene, for example. Removal of water can be performed after generation of the enamine in the tertiary amino alcohol aqueous solution, and can be performed before addition of the ketone to the tertiary amino alcohol aqueous solution.

The tertiary amino alcohol can be isolated by distillation or the like of the tertiary amino alcohol from a residual liquid after isolation of the enamine.

The isolation method of the tertiary amino alcohol according to the embodiment can be a mode of using aldehyde or can be a mode of using the ketone. The mode of generating the enamine by using the ketone is suitable since that mode is excellent in a chemical stability and an isolation operation of the tertiary amino alcohol can be performed stably.

According to the isolation method of the tertiary amino alcohol of the embodiment, the heterocyclic amine compound with a high volatility is made to react with the aldehyde or ketone to generate the imine or enamine whose vaporization under an usual temperature and a usual pressure is inhibited. Thereby, the tertiary amino alcohol can be isolated efficiently by a simple method such as distillation. Therefore, it is possible to isolate a tertiary amino alcohol efficiently and simply from a tertiary amino alcohol aqueous solution having been used as an acid gas absorbent to recover an acid gas from an exhaust gas containing the acid gas such as a carbon dioxide, for example. Thereby, the tertiary amino alcohol after isolation can be used for a recovery processing of an acid gas again.

Hereinabove, the embodiments of the present invention have been described with reference to the concrete examples, but the above-described embodiments have been presented by way of example only and are not intended to limit the present invention. Further, in the explanation of each embodiment described above, with regard to the acid gas absorbent, the acid gas removal device, and the acid gas removal method, description about a part or the like which is not directly necessary for explanation of the present invention has been omitted, but each element necessary for the above can be selected and used accordingly.

Other than the above, all the acid gas absorbents, acid gas removal devices, and acid gas removal methods which have the element of the present invention and design of which can be changed accordingly by a person skilled in the art within a scope not departing from the spirit of the present invention are comprehended by the scope of the present invention. The scope of the present invention is defined by the scope of what is claimed and the scope of an equivalent thereof.

EXAMPLE

Hereinafter, the present invention will be described more detailedly with reference to examples and comparative examples, but the present invention is not limited to those examples.

Example 1

7 g of acetone was added to a mixture of 100 g of N-methyldiethanolamine, 10 g of piperidine, and 200 g of water, and an obtained reaction solution (tertiary amino alcohol aqueous solution) was agitated for 3 hours at a room temperature. A mole ratio of acetone in relation to piperidine was acetone (mol)/piperidine (mol)=1.03. 200 g of benzene was added to the reaction solution (tertiary amino alcohol aqueous solution) after agitation, and heating to 120° C. was performed to azeotropically remove water, so that water and benzene were removed from the reaction solution. An obtained mixture of N-methyldiethanolamine and an enamine derivative of piperidine was distilled respectively under a reduced pressure, to isolate 90 g of N-methyldiethanolamine. A yield of N-methyldiethanolamine was 90% and a purity thereof was 99.2%.

Example 2

A reaction solution (tertiary amino alcohol aqueous solution) was obtained similarly to in the example 1, except that 10 g of piperazine was added instead of 10 g of piperidine and that an addition amount of acetone was changed from 7 g to 20 g in the example 1. Thereafter, similarly to in the example 1, azeotropic removal of benzene and water, and subsequently, distillation of a mixture of N-methyldiethanolamine and an enamine derivative of piperazine were performed, to isolate 92 g of N-methyldiethanolamine. A mole ratio of acetone in relation to piperazine was acetone (mol)/piperazine (mol)=2.97. A recovery rate of N-methyldiethanolamine was 92% and a purity thereof was 99.3%.

Example 3

A reaction solution (tertiary amino alcohol aqueous solution) was obtained similarly to in the example 1, except that 10 g of piperazine was added instead of 10 g of piperidine and that 12 g of acetaldehyde was added instead of 7 g of acetone in the example 1. Thereafter, similarly to in the example 1, azeotropic removal of benzene and water, and subsequently, distillation of a mixture of N-methyldiethanolamine and an imine derivative of piperazine were performed, to isolate 91 g of N-methyldiethanolamine. A mole ratio of acetaldehyde in relation to piperazine was acetaldehyde (mol)/piperazine (mol)=2.35. A recovery rate of N-methyldiethanolamine was 91% and a purity thereof was 99.1%.

Comparative Example 1

N-methyldiethanolamine was isolated similarly to in the example 1 except that acetone was not added in the example 1, and 80 g of N-methyldiethanolamine was isolated. A recovery rate of N-methyldiethanolamine was 80% and a purity thereof was 78%.

In each of the examples 1 to 3 in which aldehyde or ketone is added to the mixture of N-methyldiethanolamine and a heterocyclic amine compound, a value as high as 90% or more is obtained as the recovery rate of N-methyldiethanolamine and the purity is also as high as 99.1% or more. Thus, in the examples 1 to 3, efficient isolation of N-methyldiethanolamine is possible. On the other hand, in the comparative example 1 where neither aldehyde nor ketone is added, the recovery rate of N-methyldiethanolamine is as low as 80%, and the purity is also as low as 78%, being inferior in efficiency of isolation of N-methyldiethanolamine.

According to at least one of the embodiments of the isolation methods of the tertiary amino alcohol described hereinabove, it is possible to isolate the tertiary amino alcohol from the tertiary amino alcohol aqueous solution containing the heterocyclic amine compound by the simple method.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method for isolating a tertiary amino alcohol from a tertiary amino alcohol aqueous solution containing a heterocyclic amine compound, the method comprising:
generating an enamine by adding a ketone represented by a following general formula(2) to the tertiary amino alcohol aqueous solution,

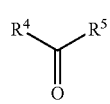

(2)

where $R^4$ and $R^5$ indicate aliphatic groups or aromatic groups having 1 to 18 carbon atoms, $R^4$ and $R^5$ may be the same or different, R⁴ and R⁵ may be joined to form a ring structure, and at least one of R⁴ and R⁵ is the aliphate group;

isolating the enamine from the tertiary amino alcohol aqueous solution; and isolating the tertiary amino alcohol from a residual liquid obtained by isolating of the enamine.

2. The method for isolating the tertiary amino alcohol according to claim 1,
wherein the isolating the enamine is performed by isolating the enamine generated in the tertiary amino alcohol aqueous solution by extraction or reduced-pressure distillation after water is distilled off from the tertiary amino alcohol aqueous solution, and
wherein the isolating the tertiary amino alcohol is performed by isolating the tertiary amino alcohol by distillation from the residual liquid obtained by isolating of the enamine.

3. The method for isolating the tertiary amino alcohol according to claim 1,
wherein the ketone is an aliphatic ketone.

4. The method for isolating the tertiary amino alcohol according to claim 1,
wherein the heterocyclic amine compound is at least one selected from the group consisting of piperidine, a piperidine derivative, piperazine and a piperazine derivative.

5. The method for isolating the tertiary amino alcohol according to claim 4,
wherein the heterocyclic amine compound is at least one selected from the group consisting of piperazine, 2-methylpiperazine, and 2,5-dimethylpiperazine.

6. The method for isolating the tertiary amino alcohol according to claim 1,
wherein the tertiary amino alcohol has an aliphatic group having 1 to 6 carbon atoms.

7. The method for isolating the tertiary amino alcohol according to claim 6,
wherein the tertiary amino alcohol is N-methyldiethanolamine.

8. The method for isolating the tertiary amino alcohol according to claim 1,
wherein the tertiary amino alcohol aqueous solution is an acid gas absorbent used in a method for removing an acid gas from a gas containing the acid gas.

9. The method for isolating the teriary amino alcohol according to claim 1 wherein said at least one of R⁴ and R⁵ is the aliphatic group having α-hydrogen.

10. The method for isolating the tertiary amino alcohol according to claim 1, wherein the ketone is at least one of acetone, ethylmethylketone, diethylketone, methylisobutylketone, cyclopentanone, cyclohexanone, and acetophenone.

* * * * *